(12) United States Patent
Drauz et al.

(10) Patent No.: US 6,437,145 B1
(45) Date of Patent: Aug. 20, 2002

(54) METHOD OF PRODUCING OXAZOLIDINONES, THE USE THEREOF AND OXAZOLIDINONES

(75) Inventors: Karlheinz Drauz, Freigericht; Günter Knaup, Bruchköbel; Stefan Retzow, Alzenau, all of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/542,278

(22) Filed: Apr. 4, 2000

Related U.S. Application Data

(62) Division of application No. 08/894,519, filed as application No. PCT/EP96/00390 on Jan. 31, 1996, now Pat. No. 6,051,715.

(30) Foreign Application Priority Data

Feb. 21, 1995 (DE) .......................................... 195 05 932

(51) Int. Cl.[7] ............................................. C07D 263/08
(52) U.S. Cl. ....................................... 548/216; 548/228
(58) Field of Search .................................. 548/216, 228

(56) References Cited

U.S. PATENT DOCUMENTS

| | | | |
|---|---|---|---|
| 4,610,983 A | 9/1986 | Takagawa et al. | 514/230 |
| 5,591,861 A | 1/1997 | Zeiss | 548/228 |
| 5,670,652 A | 9/1997 | Drauz et al. | 548/228 |

FOREIGN PATENT DOCUMENTS

| | | |
|---|---|---|
| AU | 394854 | 7/1992 |
| DE | 34 44 046 | 12/1985 |

OTHER PUBLICATIONS

Patent Abstract of Japan, vol. 6, No. 231 (C–135), Nov. 17, 1982, & JPA57 134452, Aug. 19, 1982, see Abstract.
Synthesis, No. 11, Nov. 1991, pp. 935–936, XP002005519, Lee et al., "Regioselective Amidation of Aspartic and Glutamic Acid".
Chemical Abstracts, vol. 117, No. 25, Dec. 21, 1992, Abstract No. 251789, Ascher G. & Ludescher, H., "Preparation of Aspartylphenylalanine Alkyl Esters from 5–oxo–4–oxazolideneacetates and Phenylalanine Esters", p. 740, Col. 1; XP002005520 & ATA 394 854, Jul. 10, 1992.

*Primary Examiner*—Brenda Coleman
(74) *Attorney, Agent, or Firm*—Pillsbury Winthrop LLP

(57) ABSTRACT

The invention concerns a method of producing oxazolidinones of formula (I), wherein $R^1$–$R^5$ have the meanings given in the description, by reacting cyclical anhydrides of formula (II) with carbonyl compounds of general formula (III) at temperatures between ambient temperature and approximately 150° C. The invention also concerns the production of the cyclical anhydrides of formula (II) by reacting N-protected aminodicarboxylic acids of formula (IV) with a dehydrating agent in situ. The invention further concerns the use of oxazolidinones of formula (I) for the α-selective production of esters of formula (V) and amides of general formula (VII).

15 Claims, No Drawings

METHOD OF PRODUCING OXAZOLIDINONES, THE USE THEREOF AND OXAZOLIDINONES

This is a division of application Ser. No. 09/894,519, filed Aug. 21, 1997 now U.S. Pat. No. 6,051,715 which is a national stage entry under 35 USC § 371 of PCT/EP96/00390 filed Jan. 31, 1996.

The invention is relative to methods of producing oxazolidinones of general formula I

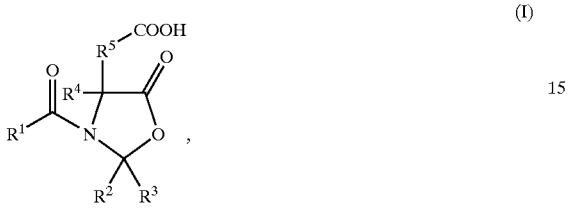

(I)

in which $R^1$ signifies hydrogen; $(C_1-C_{12})$-alkyl; $(C_2-C_{10})$-alkenyl; $(C_2-C_{10})$-alkinyl; $(C_1-C_6)$-alkyl which is substituted singly or multiply by equal or different groups from the group of halogen, $(C_1-C_4)$-alkoxy, $(C_1-C_4)$-alkylthio, —CN, $(C_2-C_5)$-alkoxycarbonyl and $(C_2-C_6)$-alkenyl; $(C_3-C_8)$-cycloalkyl which is unsubstituted or substituted by one or more groups from the group $(C_1-C_4)$-alkyl, $(C_1-C_4)$-alkoxy, $(C_1-C_4)$-alkylthio and halogen; $(C_5-C_8)$-cycloalkenyl; aryl or aryl-$(C_1-C_4)$-alkyl which are unsubstituted or substituted in the aryl group; —$OR^6$; $NR^7R^8$; or stands in conjunction with the adjacent carbonyl group for a protective group, especially boc, Z, TFA, alloc, teoc, formyl, tosyl, mesyl, fmoc, moc, suitable for protecting the amino group of an amino acid;

$R^2$ and $R^3$ signify, independently of one another and equally or differently hydrogen, $(C_1-C_8)$-alkyl or $(C_3-C_8)$-alkenyl, $(C_3-C_8)$-alkinyl or $(C_3-C_8)$-cycloallyl, which above C-containing groups can be unsubstituted or substituted singly or multiply, preferably up to three times, by equal or different groups from the group containing halogen, hydroxy, $(C_1-C_8)$-alkoxy, $(C_1-C_8)$-alkylmercapto, $(C_2-C_8)$-alkenylmercapto, $(C_2-C_8)$-alkinylmercapto, $(C_2-C_8)$-alkenyloxy, $(C_2-C_8)$-alkinyloxy, $(C_3-C_7)$-cycloalkyl, $(C_3-C_7)$-cycloalkoxy, cyano, mono- and di-$(C_1-C_4$-alkyl)-amino, aryl, aryl-$(C_1-C_6)$-alkoxy, which last two groups cited in the aryl ring can be unsubstituted or substituted singly or multiply, preferably up to three times, by equal or different groups from the group of halogen, $(C_1-C_4)$-alkyl, $(C_1-C_4)$-alkoxy, $(C_1-C_4)$-halogen alkyl, $(C_1-C_4)$-halogen alkoxy; and which groups $R^2$ and $R^3$ can be connected together to a 3-10-member ring which can also be N, O, S-heterosubstituted itself in addition to the cited substituents;

$R^4$ can be hydrogen, $(C_1-C_6)$-alkyl, $(C_2-C_6)$-alkenyl, $(C_2-C_6)$-alkinyl, aryl, alkaryl, aryl alkyl or cycloalkyl and the linear as well as the branched alkyl groups can contain halogen- and/or heteroatom substitution (N, O, S) either singly or multiply, just as the aliphatic or aromatic cycles;

$R^5$ signifies a $(C_1-C_2)$-alkane diyl chain which can be substituted with up to four $(C_1-C_4)$-alkyl groups, $(C_3-C_4)$-alkenyl groups, $(C_3-C_4)$-alkinyl groups, $(C_3-C_8)$-cycloalkyl groups and/or aryl groups, which alkane diyl chain itself as well as its substituents can be N, O, S-heterosubstituted and two of the substituents of the alkane diyl chain can be connected to one another or one of the substituents of the alkane diyl chain with $R^4$ even to a ring;

$R^6$ signifies hydrogen, $(C_1-C_8)$-alkyl, $(C_3-C_{12})$-cycloalkyl, $(C_2-C_8)$-alkenyl or $(C_2-C_8)$-alkinyl, which above C-containing groups are unsubstituted or substituted singly or multiply, preferably up to three times, by equal or different groups from the group containing halogen, hydroxy, $(C_1-C_8)$-alkoxy, $(C_1-C_8)$-alkylmercapto, $(C_2-C_8)$-alkenylmercapto, $(C_2-C_8)$-alkinylmercapto, $(C_2-C_8)$-alkenyloxy, $(C_2-C_8)$-alkinyloxy, $(C_3-C_7)$-cyClOalkyl, $(C_3-C_7)$-cycloalkoxy, cyano, mono-and di-$(C_1-C_4$-alkyl)-amino, carboxy, $(C_1-C_8)$-alkoxycarbonyl, $(C_2-C_8)$-alkenyloxycarbonyl, $(C_1-C_8)$-alkylmercaptocarbonyl, $(C_2-C_8)$-alkinyloxycarbonyl, $(C_1-C_8)$-alkylcarbonyl, $(C_2-C_8)$ alkenylcarbonyl, $(C_2-C_8)$-alkinylcarbonyl, 1-(hydroxy imino)-$(C_1-C_6)$-alkyl, 1-[$(C_1-C_4)$-alkylimino]-$(C_1-C_4)$-alkyl, 1-[$(C_1-C_4)$-alkoxyimino]-$(C_1-C_6)$-alkyl, $(C_1-C_8)$-alkylcarbonyl amino, $(C_2-C_8)$-alkenylcarbonyl amino, $(C_2-C_8)$-alkinylcarbonyl amino, amino carbonyl, $(C_1-C_8)$-alkylamino carbonyl, di-$(C_1-C_6)$-alkylamino carbonyl, $(C_2-C_6)$-alkenylamino carbonyl, $(C_2-C_6)$-alkinylamino carbonyl, $(C_1-C_8)$-alkoxycarbonyl amino, $(C_1-C_8)$-alkylamino carbonyl amino, $(C_1-C_6)$-alkylcarbonyloxy, which is unsubstituted or substituted by halogen, nitro, $(C_1-C_4)$-alkoxy or optionally substituted phenyl, $(C_2-C_6)$-alkenylcarbonyloxy, $(C_2-C_6)$-alkinylcarbonyloxy, $(C_1-C_8)$-alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonyl amino, phenyl-$(C_1-C_6)$-alkylcarbonyl amino, which last-named 9 groups in the phenyl ring are unsubstituted or substituted simply or multiply, preferably up to three times, by equal or different groups from the group of halogen, $(C_1-C_4)$-alkyl, $(C_1-C_4)$-alkoxy, $(C_1-C_4)$-halogen alkyl, $(C_1-C_4)$-halogen alkoxy and nitro, and [containing] groups of the formulas —$SiR'_3$, —$O$—$SiR'_3$, $R'_3Si$—$(C_1-C_8)$-alkoxy, —$CO$—$O$—$NR'_2$, —$O$—$N$=$CR'_2$, —$N$=$CR'_2$, —$O$—$NR'_2$, $CH(OR')_2$ and —$O$—$(CH_2)_m$—$CH(OR')_2$ in which the R's in the cited formulas signify independently of each other hydrogen, $(C_1-C_4)$-alkyl, phenyl, which is unsubstituted or substituted singly or multiply, preferably up to three times, by equal or different groups from the group of halogen, $(C_1-C_4)$-alkyl, $(C_1-C_4)$-alkoxy, $(C_1-C_4)$-halogen alkyl, $(C_1-C_4)$-halogen alkoxy and nitro, or signify in pairs a $(C_2-C_6)$-alkane diyl chain and m=0 to 6, and [containing] a substituted alkoxy group of the formula R"$O$—$CHR'''(OR")$—$(C_1-C_6)$-alkoxy in which the R" signify independently of each other $(C_1-C_4)$-alkyl or together $(C_1-C_6)$-alkane diyl and R"" signifies hydrogen or $(C_1-C_4)$-alkyl, and $R^7$ and $R^8$ have a significance, independently of one another and equally or differently, indicated for $R^6$ and $R^7$ and $R^8$ can also be connected among themselves to a ring;

as well as is relative, e.g., to novel oxazolidinones obtainable according to the method of the invention and to the use of oxazolidinones.

1,3-oxazolidin-5-ones are especially significant as activated intermediates in the α-selective reaction of α-amino dicarboxylic acids with nucleophiles. Esters or amides can be produced from α-amino dicarboxylic acids by reacting oxazolidinones with alcohols or amines in approximately 100% α-regioselectivity under almost complete preservation of the optical activity of the initial product at the same time, that is, with decidedly high enantioselectivity.

α-acid derivatives of aspartic acid and glutamic acid are used as pharmaceutical agents such as e.g. CCK antagonists (Drugs of the Future, 1993, 18, 919–31) and as sweeteners such as e.g. alitame (EP 34,876), aspartame (DE 21 07 411) and L-Asp-D-α-amino alkanoyl-(S)-(α-alkylbenzyl amides (WO 94/00028).

A protection of the β- and γ-carboxyl function such, e.g., as ester is necessary for the α-selective production of these substances. If this does not take place, mixtures of α- and β- and/or γ-substitution products result which must be purified in an expensive manner. This is the case if the readily producible inner anhydrides of general formula II are used for coupling (Houben-Weyl, volume 15/1, J. Chem. Soc. 1950, 1954, J. Chem. Soc. 1952, 24, DE 21 07 411, WO 87/03869).

The invention had the problem of developing a method permitting an α-selective coupling of Asp and Glu using the relatively simply producible inner anhydrides. Furthermore, the invention had the problem of indicating novel N-acylated oxazolidinone derivatives which should permit as intermediate products the α-selective coupling with amines or alcohols with the obtention of esters and amides from α-amino dicarboxylic acids.

These and other problems not cited in detail are solved with a method by reacting cyclic anhydrides of general formula II

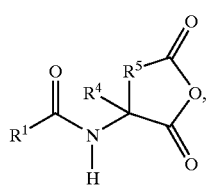

(II)

in which $R^1$, $R^4$ and $R^5$ have the significance indicated for formula I with carbonyl compounds of general formula III

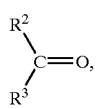

(III)

in which $R^2$ and $R^3$ have the significance indicated for formula I, or with compounds which produce, as precursors of the compounds of formula III under the conditions of the reaction, compounds of formula III during the reaction at temperatures between room temperature and approximately 150° C., preferably in the presence of catalytic amounts of acids.

In a preferred embodiment of the invention the cyclic anhydrides of general formula II can be obtained by reacting N-protected amino dicarboxylic acids of general formula IV

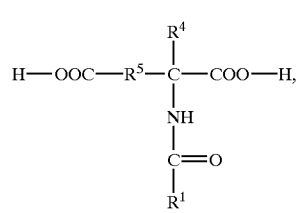

(IV)

in which $R^1$, $R^4$ and $R^5$ have the significance indicated for formula I with a dehydrating agent at temperatures between −20° C. and approximately 150° C. According to the invention it is not necessary thereby to isolate the inner anhydrides of general formula II, but rather they can be produced in situ.

Thus, in the above-named variant the oxazolidinone of general formula I can be obtained directly from the α-amino dicarboxylic acids of general formula IV without taking the path via the isolation of the anhydride according to formula II. If, on the other hand, the anhydride of general formula II accumulates in a synthetic process, the target product of formula I striven for can be produced starting from the latter in likewise high yield and purity.

In an advantageous method variant all substances commonly known to an expert in the art can be used as dehydrating agents which substances can bring about the formation of an inner anhydride from a dicarboxylic acid. The dehydrating agents which can be used in the reaction of the invention include, among others, phosphorus pentoxide, thioyl chloride, orthoester, acetic hydride, etc. Acetic anhydride is especially preferred.

It has proven to be advantageous for the method of the invention to carry out the reaction in an organic solvent. All organic solvents which are inert under the reaction conditions to the reactants are suitable as solvent. Due to their good solvent power for anhydrides, organic carboxylic acids or their derivatives are especially preferred. Carboxylic acids with 1 to 5 C atoms are particularly preferred. Acetic acid is an especially preferred solvent.

The reaction for producing the N-acyl oxazolidinones of general formula I is preferably carried out at elevated temperatures between 50 and 150° C. A temperature range between 70 and 120° C. has proven to be especially advantageous.

All protonic acids and Lewis acids can be used as catalytically active acid within the framework of the invention. The following are possible, among others: Sulfuric acid, hydrochloric acid, trifluoroacetic acid, sulfonic acids, p-TosOH, etc. Sulfonic acids are preferable and p-TosOH is especially preferable.

The method of the invention can be carried out with special success in the case of those compounds of formulas II or IV in which $R^4$ stands for H and $R^5$ for —$CH_2$— or —$CH_2$—$CH_2$—. In the case of $R^5$=—$CH_2$— derivatives of aspartic acid are present and in the case of $R^5$=—$CH_2$—$CH_2$— derivatives of glutamic acid or of the particular cyclic anhydrides are present.

Furthermore, it is also particularly advantageous within the framework of the invention that compounds are reacted in which $R^1$ stands for H, that is, the α-amino group is formyl-protected.

In addition, it is preferred in a further special method variant of the invention to react compounds of formula III in which $R^2$ and $R^3$ are hydrogen. Although it is possible according to the invention and is also preferred in many instances to use any ketones or aldehydes as carbonyl, compounds, the realization of the invention succeeds especially well if formaldehyde is used. In addition, formaldehyde has the additional advantage that it can also be used as a readily manageable depot form.

Thus, any depot form releasing formaldehyde in the actual reaction can be used as precursor of formaldehyde. Paraformaldehyde or trioxane, among others, are preferred. The splitting of these depot forms under the conditions of the reaction takes place acidically with a protonic acid or Lewis acid preferably used as catalyst for the splitting. Sulfonic acids, p-TosOH, trifluoroacetic acid, thionyl chloride, sulfuric acid, etc., among others, are possible. P-TosOH is preferred.

Novel oxazolidinones of general formula I also constitute subject matter of the invention

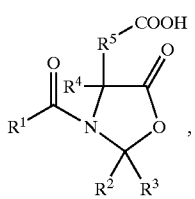

(I)

in which

R$^1$ is hydrogen;

R$^2$ and R$^3$ signify, independently of one another and equally or differently hydrogen, (C$_1$–C$_8$)-alkyl or (C$_3$–C$_8$)-alkenyl, (C$_3$–C$_8$)-alkinyl or (C$_3$–C$_8$)-cycloalkyl, which above C-containing groups can be unsubstituted or substituted singly or multiply, preferably up to three times, by equal or different groups from the group containing halogen, hydroxy, (C$_1$–C$_8$)-alkoxy, (C$_1$–C$_8$)-alkylmercapto, (C$_2$–C$_8$)-alkenylmercapto, (C$_2$–C$_8$)-alkinylmercapo, (C$_2$–C$_8$)-alkenyloxy, (C$_2$–C$_8$)-alkinyloxy, (C$_3$–C$_7$)-cycloalkyl, (C$_3$–C$_7$)-cycloalkoxy, cyano, mono- and di-(C$_1$–C$_4$-alkyl)-amino, aryl, aryl-(C$_1$–C$_6$)-alkoxy, which last two groups cited in the phenyl ring can be unsubstituted or substituted singly or multiply, preferably up to three times, by equal or different groups from the group of halogen, (C$_1$–C$_4$)-alkyl, (C$_1$–C$_4$)-alkoxy, (C$_1$–C$_4$)-halogen alkyl, (C$_1$–C$_4$)-halogen alkoxy; and which groups R$^2$ and R$^3$ can be connected together to a 3-10-member ring which can also be N, O, S-heterosubstituted itself in addition to the cited substituents;

R$^4$ can be hydrogen, (C$_1$–C$_6$)-alkyl, (C$_2$–C$_6$)-alkenyl, (C$_2$–C$_6$)-alkinyl, aryl, alkaryl, aryl alkyl or cycloalkyl and the linear as well as the branched alkyl groups can contain halogen- and/or heteroatom substitution (N, O, S) either singly or multiply, just as the aliphatic or aromatic cycles;

R$^5$ signifies a (C$_1$–C$_2$)-alkane diyl chain which can be substituted with up to four (C$_1$–C$_4$)-alkyl groups, (C$_3$–C$_4$)-alkenyl groups, (C$_3$–C$_4$)-alkinyl groups, (C$_3$–C$_8$)-cycloalkyl groups and/or aryl groups, which alkane diyl chain itself as well as its substituents can be N, O, S-heterosubstituted and two of the substituents of the alkane diyl chain can be connected to one another or one of the substituents of the alkane diyl chain with R$^4$ even to a ring; with the exception of the oxazolidinone of formula I with R$^2$=H, R$^3$=CCl$_3$, R$^5$=CH$_2$ and R$^4$=H.

Oxazolidinones in which R$^4$ is hydrogen and R$^5$ is —CH$_2$— or —CH$_2$—CH$_2$— are preferred.

Oxazolidinones in which R$^2$ and R$^3$ are each hydrogen are also preferred.

Subject matter of the invention is also constituted by oxazolidinones of general formula I in which R$^1$ is aryl and the aromatic ring can carry halogen or other substituents up to threefold and R$^2$–R$^4$ are hydrogen and R$^5$ is —CH$_2$— or —CH$_2$—CH$_2$—.

The novel oxazolidinones are coupled in an especially advantageous manner in the presence of an auxiliary base e.g. with protected amino acids, yielding α-selectively N-acyl-protected coupling products. Although the coupling products can be produced e.g. even without the use of the oxazolidinones of general formula I produced in accordance with the invention or of the novel oxazolidinones of general formula I in accordance with the invention, the use of the oxazolidinones in accordance with the invention is preferred since the α-selectivity e.g. in the coupling of compounds of general formula II with alcohols or amines is distinctly below 100% and in many instances only at about 80% or less.

Therefore, the invention also has as subject matter the use of oxazolidinones indicated herein for the α-selective production of esters of general formula V

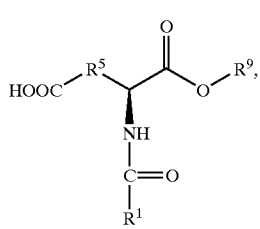

(V)

in which R$^1$ and R$^5$ have the significance indicated for formula I and

R$^9$ signifies hydrogen, (C$_1$–C$_{18}$)-alkyl, (C$_3$–C$_{12}$)-cycloalkyl, (C$_2$–C$_8$)-alkenyl or (C$_2$–C$_8$)-alkinyl, which above C-containing groups are unsubstituted or substituted singly or multiply, preferably up to three times, by equal or different groups from the group containing halogen, hydroxy, (C$_1$–C$_8$)-alkoxy, (C$_1$–C$_8$)-alkylmercapto, (C$_2$–C$_8$)-alkenylmercapto, (C$_2$–C$_8$)-alkinylmercapto, (C$_2$–C$_8$)-alkenyloxy, (C$_2$–C$_8$)-alkinyloxy, (C$_3$–C$_7$)-cycloalkyl, (C$_3$–C$_7$)-cycloalkoxy, cyano, mono- and di-(C$_1$–C$_4$-alkyl)-amino, carboxy, (C$_1$–C$_8$)-alkoxycarbonyl, (C$_2$–C$_8$)-alkenyloxycarbonyl, (C$_1$–C$_8$)-alkylmercaptocarbonyl, (C$_2$–C$_8$)-alkinyloxycarbonyl, (C$_1$–C$_8$)-alkylcarbonyl, (C$_2$–C$_8$) alkenylcarbonyl, (C$_2$–C$_8$)-alkinylcarbonyl, 1-(hydroxy imino)-(C$_1$–C$_6$)-alkyl, 1-[(C$_1$–C$_4$)-alkylimino]-(C$_1$–C$_4$)-alkyl, 1-[(C$_1$–C$_4$)-alkoxyimino]-(C$_1$–C$_6$)-alkyl, (C$_1$–C$_8$)-alkylcarbonyl amino, (C$_2$–C$_8$)-alkenylcarbonyl amino, (C$_2$–C$_8$)-alkinylcarbonyl amino, amino carbonyl, (C$_1$–C$_8$)-alkylamino carbonyl, di-(C$_1$–C$_6$)-alkylamino carbonyl, (C$_2$–C$_6$)-alkenylamino carbonyl, (C$_2$–C$_6$)-alkinylamino carbonyl, (C$_1$–C$_8$)-alkoxycarbonyl amino, (C$_1$–C$_8$)-alkylamino carbonyl amino, (C$_1$–C$_6$)-alkylcarbonyloxy, which is unsubstituted or substituted by halogen, nitro, (C$_1$–C$_4$)-alkoxy or optionally substituted phenyl, (C$_2$–C$_6$)-alkenylcarbonyloxy, (C$_2$–C$_6$)-alkinylcarbonyloxy, (C$_1$–C$_8$)-alkylsulfonyl, phenyl, phenyl-(C$_1$–C$_6$)-alkoxy, phenyl-(C$_1$–C$_6$)-alkoxycarbonyl, phenoxy, phenoxy-(C$_1$–C$_6$)-alkoxy, phenoxy-(C$_1$–C$_6$)-alkoxycarbonyl, phenylcarbonyloxy, phenylcarbonyl amino, phenyl-(C$_1$–C$_6$)-alkylcarbonyl amino, which last-named 9 groups in the phenyl ring are unsubstituted or substituted simply or multiply, preferably up to three times, by equal or different groups from the group of halogen, $(C_1-C_4)$-alkyl, $(C_1-C_4)$-alkoxy, $(C_1-C_4)$-halogen alkyl, $(C_1-C_4)$-halogen alkoxy and nitro, and [containing] groups of the formulas —$SiR'_3$, —O—$SiR'_3$, $R'_3Si$—$(C_1-C_8)$-alkoxy, —CO—O—$NR'_2$, —O—N=$CR'_2$, —N=$CR'_2$, —O—$NR'_2$, $CH(OR')_2$ and —O—$(CH_2)_m$—$CH(OR')_2$ in which the R's in the cited formulas signify independently of each other hydrogen, $(C_1-C_4)$-alkyl, phenyl, which is unsubstituted or substituted singly or multiply, preferably up to three times, by equal or different groups from the group of halogen, $(C_1-C_4)$-alkyl, $(C_1-C_4)$-alkoxy, $(C_1-C_4)$-halogen alkyl, $(C_1-C_4)$-halogen alkoxy and nitro, or signify in pairs a $(C_2-C_6)$-alkane diyl chain and m=0 to 6, and [containing] a substituted alkoxy group of the formula R"O—CHR'"(OR")—$(C_1-C_6)$-alkoxy in which the R" signify independently of each other $(C_1-C_4)$-alkyl or together $(C_1-C_6)$-alkane diyl and R"" signifies hydrogen or $(C_1-C_4)$-alkyl,
by reaction with alcohols of general formula VI

(VI)

in which $R^9$ has the significance indicated for formula V in an organic solvent in the presence of a base.

In addition thereto, the invention also comprises the use of the oxazolidinones of general formula produced or defined herein for the α-selective production of amides of general formula VII

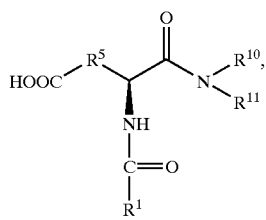

(VII)

in which $R^1$ and $R^5$ have the significance indicated for formula I and $R^{10}$ and $R^{11}$ have the significance, independently of one another and equally or differently, of $R^9$ and can, moreover, be combined with one another to a ring
by reaction with amines with amines of general formula VIII

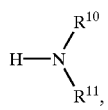

(VIII)

in which $R^{10}$ and $R^{11}$ have the significance indicated for formula VII in an organic solvent in the presence of a base.

The use of the oxazolidinones of the invention for producing amides by reaction with amines of general formula VIII with formula VIII standing for L-phenylalaninemethyl ester, D-alanine-2,2,4,4-tetramethylthietan-3-yl amide or D-amino butyric acid-(2S)-phenyl-propanamide or in which $R^{10}=R^{11}$=n-pentyl or $R^{10}$=n-pentyl and $R^{11}$=3-methoxy-n-propyl is especially preferred.

Thus, the invention also finally comprises a method for the α-selective production of esters and amides of general formula V or VII which is characterized in that N-acyl-oxazolidinones of general formula I are brought to reaction with alcohols or amines of general formula VI or VIII in an organic solvent in the presence of an auxiliary base and that in order to produce the oxazolidinone of general formula I aldehydes or ketones of general formula III are reacted with N-acyl-amino acid anhydrides of general formula II at rather high temperatures, preferably 50° C., especially preferably temperatures above 50° C. and quite especially preferably temperatures above 100° C., preferably in the presence of a catalytic amount of acids. In addition, the amino acids of general formula IV can be brought to a reaction with aldehydes or ketones of general formula III.

In a preferred method variant of the invention an inert organic solvent is used in which oxazolidinones of general formula I and alcohols or amines of general formulas VI and VIII dissolve to an extent sufficient for the course of the reaction, preferably ether, halogenated solvents or sterically exacting alcohols, with iospropanol or 2-butanol being especially preferred.

In an advantageous method variant all basic compounds can be used as base which dissolve in the organic solvent in which the reaction takes place and which do not react themselves with the oxazolidinone of general formula I as well as which have a base strength sufficient for deprotonizing the oxazolidinone of general formula I on the carboxyl function. Tert. amines are preferred and triethylamine or tributylamine are especially preferred.

Finally, all organic solvents in which the anhydrides of formula II dissolve can be considered favorably as organic solvents of the reaction for producing oxazolidinone. Short-chain carboxylic acids are preferred and acetic acid is quite especially preferred.

An economical and universally applicable method was found therewith in a totally surprising and unexpected manner for coupling, among others, aspartic acid and glutamic acid α-selectively via the anhydride route with nucleophiles. In an advantageous modification of this method the amino dicarboxylic acid anhydrides are reacted in an organic solvent with the assistance of catalytic amounts of a strong acid with aldehydes or ketones. The oxazolidinone obtained in this manner can be coupled e.g. in the presence of a base with L-Phe-OMe. Formyl-aspartame is α-selectively obtained. According to the state of the art formyl-Asp-anhydride has been used up to the present in the aspartame process as a reactive intermediate stage which only permits a regioisomeric ratio of α-formyl-aspartame/β-formyl-aspartame like 80/20.

The method of the invention is used with particular advantage for producing oxazolidinones of aspartic acid. These compounds have a significant position as intermediate stage for dipeptide sweeteners.

Furthermore, it is preferred according to the invention to heat a formyl amino acid anhydride of general formula II in glacial acetic acid with paraformaldehyde in the presence of catalytic amounts of paratoluene sulfonic acid to 100° C. This strategy allows the complete reaction of the anhydride to the oxazolidinone of general formula I ($R^2$, $R^3$=H). The following example explains the invention:

EXAMPLE 1

Production of 4-carboxymethyl-3-formyl-1,3-oxazolidin-5-one 14.3 g (100 mmol) of formyl aspartic acid anhydride are charged into a 100° C. solution of 9 g (300 mmol) paraformaldehyde in 200 ml glacial acetic acid. After 30 min the mixture is cooled to 50° C. and the acetic acid removed in a vacuum. Then, the yellowish oily residue is taken up in a little saturated sodium hydrogen carbonate solution and extracted several times after acidification of the aqueous solution to pH 1.5 with ethyl acetate. The collected organic phases are dried over magnesium sulfate and then filtered. After removal of the solvent in a vacuum a yellowish oil is obtained.

Production of α-formyl Aspartic Acid Benzyl Amide

The yellowish oil of example 1, dissolved in 100 ml isopropanol, is compounded with 14 ml (100 mmol) triethylamine and compounded with 10 ml (100 mmol) benzylamine. The mixture is heated for 3 h to 50° C. After removal of the isopropanol in a vacuum the residue is taken up in 100 ml 1 N HCl, agitated 1 h and then extracted several times with ethyl acetate. The saturated organic phases are dried over magnesium sulfate and after filtration the solvent is removed in a vacuum. 20 g (80 mmol) 80% of a slightly yellowish solid is obtained.

EXAMPLE 2

Production of α-formyl Aspartic Acid Methyl Ester 1 equiv. Of a solution of NaOMe in MeOH is added dropwise to a solution of For-oxazolidinone (~100 mmol) in methanol (50 ml) at −10° C. The solution is then put on 1 N HCl (100 ml) and extracted twice with ethyl acetate (100 ml). The organic phases are dried over magnesium sulfate and the residue obtained after removal of the solvent in a vacuum is purified on silica gel. The α-methyl ester of For-aspartic acid is obtained in 80% yield.

What is claimed is:
1. A method of producing oxazolidinones of formula

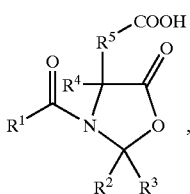

(I)

in which
R$^1$ signifies hydrogen; $(C_1-C_{12})$-alkyl; $(C_2-C_{10})$-alkenyl; $(C_2-C_{10})$-alkinyl; $(C_1-C_6)$-alkyl which is substituted singly or multiply by the same or different groups selected from the group consisting of halogen, $(C_1-C_4)$-alkoxy, $(C_1-C_4)$-alkylthio, —CN, $(C_2-C_5)$-alkoxycarbonyl and $(C_2-C_6)$-alkenyl; $(C_3-C_8)$-cycloalkyl which is unsubstituted or substituted by one or more groups selected from the group consisting of $(C_1-C_4)$-alkyl, $(C_1-C_4)$-alkoxy, $(C_1-C_4)$-alkylthio and halogen; $(C_5-C_8)$-cycloalkenyl; aryl or aryl-$(C_1-C_4)$-alkyl which are unsubstituted or substituted in the aryl group; —OR$^6$; NR$^7$R$^8$; or stands in conjunction with the adjacent carbonyl group for a protective group selected from the group consisting of boc, Z, TFA, alloc, teoc, formyl, fmoc and moc, for protecting the amino group of an amino acid;

R$^2$ and R$^3$ may be the same or different and signify, independently of one another, hydrogen, $(C_1`C_8)$-alkyl or $(C_3-C_8)$-alkenyl, $(C_3-C_8)$-alkinyl or $(C_3-C_8)$-cycloalkyl, which above C-containing groups are unsubstituted or substituted singly or multiply, up to three times, by the same or different groups selected from the group consisting of halogen, hydroxy, $(C_1-C_8)$-alkoxy, $(C_1-C_8)$-alkylmercapto, $(C_2-C_8)$-alkenylmercapto, $(C_2-C_8)$-alkinylmercapto, $(C_2-C_8)$-alkenyloxy, $(C_2-C_8)$-alkinyloxy, $(C_3-C_7)$-cycloalkyl, $(C_3-C_7)$-cycloalkoxy, cyano, mono- and di-$(C_1-C_4$alkyl)-amino, aryl and aryl-$(C_1-C_6)$-alkoxy, in which the aryl groups can be unsubstituted or substituted singly or multiply, up to three times, by the same or different groups selected from the group consisting of halogen, $(C_1-C_4)$-alkyl, $(C_1-C_4)$-alkoxy, $(C_1-C_4)$-halogen alkyl and $(C_1-C_4)$-halogen alkoxy; and which groups R$^2$ and R$^3$ can be connected together to form a 3-10-member ring which can contain an N, O, or S-heterosubstitution in addition to the cited substituents;

R$^4$ signifies hydrogen, $(C_1-C_6)$-alkyl, $(C_2-C_6)$-alkenyl, $(C_2-C_6)$-alkinyl, aryl, alkaryl, aralkyl, or cycloalkyl;

R$^5$ signifies a $(C_1-C_2)$-alkane diyl chain which can be substituted with up to four groups selected from the group consisting of $(C_1-C_4)$-alkyl groups, $(C_3-C_4)$-alkenyl groups, $(C_3-C_4)$-alkinyl groups, $(C_3-C_8)$-cycloalkyl groups and aryl groups, which alkane diyl chain and its substituents can be N, O, S-heterosubstituted in lieu of a carbon atom; and two of the substituents of the alkane diyl chain can be connected to one another or to one of the substituents of the alkane diyl chain with an R$^4$ group optionally to form a ring structure;

R$^6$ signifies hydrogen, $(C_1-C_{18})$-alkyl, $(C_3-C_{12})$-cycloalkyl, $(C_2-C_8)$-alkenyl or $(C_2-C_8)$-alkinyl, which above C-containing groups are unsubstituted or may be substituted singly or multiply, up to three times, by one or more moieties selected from the group consisting of: halogen, hydroxy, $(C_1-C_8)$-alkoxy, $(C_1-C_8)$-alkylmercapto, $(C_2-C_8)$-alkenylmercapto, $(C_2-C_8)$-alkinylmercapto, $(C_2-C_8)$-alkenyloxy, $(C_2-C_8)$-alkinyloxy, $(C_3-C_7)$-cycloalkyl, $(C_3-C_7)$-cycloalkoxy, cyano, mono- and di-$(C_1-C_4$-alkyl)-amino, carboxy, $(C_1-C_8)$-alkoxycarbonyl, $(C_2-C_8)$-alkenyloxycarbonyl, $(C_1-C_8)$-alkylmercaptocarbonyl, $(C_2-C_8)$-alkinyloxycarbonyl, $(C_1-C_8)$-alkylcarbonyl, $(C_2-C_8)$ alkenylcarbonyl, $(C_2-C_8)$-alkinylcarbonyl, 1-(hydroxy imino)-$(C_1-C_6)$-alkyl, 1-{$(C_1-C_4)$-alkylimino}-$(C_1-C_4)$-alkyl, 1-{$(C_1-C_4)$-alkoxyimino}$(C_1-C_6)$-alkyl, $(C_1-C_8)$-alkylcarbonyl amino, $(C_2-C_8)$-alkenylcarbonyl amino, $(C_2-C_8)$-alkinylcarbonyl amino, amino carbonyl, $(C_1-C_8)$-alkylamino carbonyl, di-$(C_1-C_6)$-alkylamino carbonyl, $(C_2-C_6)$-alkenylamino carbonyl, $(C_2-C_6)$-alkinylamino carbonyl, $(C_1-C_8)$-alkoxycarbonyl amino, $(C_1-C_8)$-alkylamino carbonyl amino, $(C_1-C_6)$-alkylcarbonyloxy, which is unsubstituted or substituted by halogen, nitro, $(C_1-C_4)$-alkoxy or optionally substituted phenyl, $(C_2-C_6)$-alkenylcarbonyloxy, $(C_2-C_6)$-alkinylcarbonyloxy, $(C_1-C_8)$-alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonyl amino, phenyl-$(C_1-C_6)$-alkylcarbonyl amino;

in which the phenyl rings of said moieties are independently unsubstituted or substituted singly or multiply, up to three times, by groups that are the same or different and are selected from the group consisting of halogen, $(C_1-C_4)$-alkyl, $(C_1-C_4)$-alkoxy, $(C_1-C_4)$-halogen alkyl, $(C_1-C_4)$-halogen alkoxy and nitro, and groups of formulas —SiR'$_3$, —O—SiR'$_3$, R'$_3$Si—$(C_1-C_8)$-alkoxy, —CO—O—NR'$_2$, —O—N=CR'$_2$, —N=CR'$_2$, —O—NR'$_2$, CH(OR')$_2$ and —O—$(CH_2)_m$—CH(OR')$_2$ each R' signifies, independently of each other R', hydrogen, $(C_1-C_4)$-alkyl, phenyl, which is unsubstituted or substituted singly or multiply, up to three times, by groups that are the same or different selected from the group consisting of halogen, $(C_1-C_4)$-alkyl, $(C_1-C_4)$-alkoxy, $(C_1-C_4)$-halogen alkyl, $(C_1-C_4)$-halogen alkoxy and nitro, or signify in pairs a $(C_2-C_6)$-alkane diyl chain, and m=0 to 6; and $R^7$ and $R^8$ are the same or different and signify independently of one, the same groups as are indicated for $R^6$ and $R^7$ and $R^8$ also are optionally connected among themselves to form a ring;

by reacting cyclic anhydrides of formula II

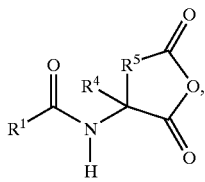
(II)

in which $R^1$, $R^4$ and $R^5$ have the significance indicated for formula I, with carbonyl compounds of formula III

(III)

in which $R^2$ and $R^3$ have the significance indicated for formula I, or with compounds which produce, as precursors of the compounds of formula III under the conditions of the reaction, compounds of formula III during the reaction at temperatures between room temperature and approximately 150° C.

2. The method according to claim 1, wherein compounds of formula II

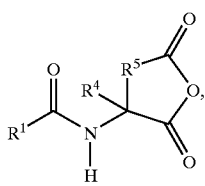
(II)

in which $R^1$, $R^4$ and $R^5$ have the significance indicated for formula I are produced by reacting N-protected amino dicarboxylic acids of formula IV

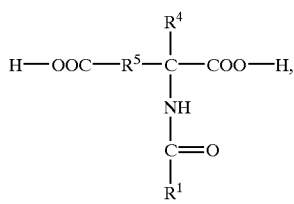
(IV)

in which $R^1$, $R^4$ and $R^5$ have the significance indicated for formula I with a dehydrating agent in situ.

3. The method according to claim 2, wherein acetic anhydride is used as the dehydrating agent.

4. The method according to claim 1, wherein the reaction is carried out in an organic solvent.

5. The method according to claim 4, wherein the solvent comprises carboxylic acids with 1 to 5 carbon atoms.

6. The method according to claim 1, wherein the reaction is carried out at temperatures between 500° and 150° C.

7. The method according to claim 1, wherein the reaction is carried out in the presence of catalytic amounts of acids.

8. The method according to claim 1, wherein in the compounds of formula II, $R^4$ signifies H and $R^5$ signifies —$CH_2$— or —$CH_2$—$CH_2$—.

9. The method according to claim 1, wherein in the compounds of formula II, $R^1$ signifies H.

10. The method according to claim 1, wherein in the compounds of formula III, $R^2$ and $R^3$ are hydrogen.

11. The method according to claim 10, wherein paraformaldehyde or trioxane is used as a precursor of formaldehyde.

12. The method according to claim 11, wherein splitting the precursor of the formaldehyde is catalyzed acidically.

13. The method according to claim 12, wherein splitting the precursor is catalyzed with p-TosOH.

14. The method according to claim 1, wherein linear or branched alkyl groups of $R^4$ each independently contain at least one substituent selected from the group consisting of a halogen and a heteroatom substitution in lieu of a carbon, wherein the heteroatom is selected from the group consisting of N, O and S.

15. The method according to claim 6, wherein the reaction is carried out at temperatures between 70° and 120° C.

\* \* \* \* \*